United States Patent [19]

Kristinsson et al.

[11] Patent Number: 4,783,468
[45] Date of Patent: Nov. 8, 1988

[54] INSECTICIDAL 5-PYRIMIDINE CARBONITRILES

[75] Inventors: Haukur Kristinsson, Basel; Odd Kristiansen, Möhlin, both of Switzerland

[73] Assignee: Ciba-Geigy Corporation, Ardsley, N.Y.

[21] Appl. No.: 41,163

[22] Filed: Apr. 22, 1987

[30] Foreign Application Priority Data

Apr. 30, 1986 [CH] Switzerland ............ 1772/86-6

[51] Int. Cl.$^4$ .................... A01N 43/54; C07G 239/46
[52] U.S. Cl. .................... 514/275; 544/243; 544/320; 544/321; 544/323
[58] Field of Search ............ 544/323, 248, 320, 321; 514/275

[56] References Cited

U.S. PATENT DOCUMENTS 4,092,150  5/1978  Treves ......................... 544/320
4,116,674  9/1978  Sunley et al. ................ 544/321

FOREIGN PATENT DOCUMENTS 0084758  1/1982  European Pat. Off. ......... 544/320

Primary Examiner—Mary C. Lee
Assistant Examiner—Zinna Northington
Attorney, Agent, or Firm—Kevin T. Mansfield; Edward McC. Roberts

[57] ABSTRACT

The invention relates to novel substituted 2,4-diamino-5-cyano-pyrimidines of formula

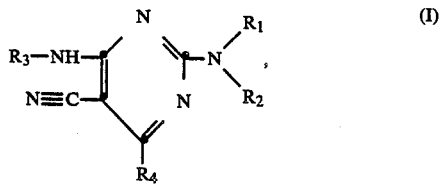

wherein
$R_1$ is hydrogen, $C_1$-$C_6$alkyl, $C_2$-$C_6$alkenyl or $C_2$-$C_6$alkynyl,
$R_2$ is hydrogen, $C_1$-$C_{10}$alkyl or $C_3$-$C_6$cycloalkyl, or
$R_1$ and $R_2$, when taken together, are a radical selected from the group consisting of—$(CH_2)_3$—,—$(CH_2)_4$— and—$(CH_2)_5$,
$R_5$ is hydrogen or a radical—CO—$R_5$ or—$SO_2$—$R_6$,
$R_4$ is a radical selected from the group consisting of —$NH_2$,—NH—CO—$R_5$,—NH—$SO_2$—$R_6$,

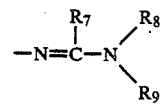

or —NH—CH=N—$R_{10}$;
$R_5$ is hydrogen, $C_1$-$C_{12}$alkyl, $C_3$-$C_6$cycloalkyl, $C_1$-$C_6$alkoxy, perhalogenated $C_1$-$C_3$alkyl or the radical

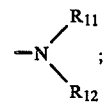

$R_6$ is $C_1$-$C_6$alkyl,
$R_7$ is hydrogen or $C_1$-$C_6$alkyl,
$R_8$ and $R_9$ are each independently of the other hydrogen or $C_1$-$C_6$alkyl or, when taken together, are a radical selected from the group consisting of—$(CH_2)_3$—,—$(CH_2)_4$—and—$(CH_2)_5$,
$R_{10}$ is a radical—$SO_2$—$R_{13}$ or

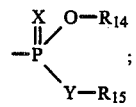

$R_{11}$ and $R_{12}$ are each independently of the other hydrogen or $C_1$-$C_6$-alkyl or, when taken together, are a radical selected from the group consisting of—$(CH_2)_3$—,—$(CH_2)_4$—and—$(CH_2)_5$,
$R_{13}$ is $C_1$-$C_{10}$alkyl, $C_1$-$C_{10}$alkyl which is substituted by up to 10 halogen atoms, or is $C_3$-$C_6$cycloalkyl
$R_{14}$ and $R_{15}$ are each independently of the other $C_1$-$C_{10}$alkyl; and
X and Y are each independently of the other oxygen or sulfur, and salts thereof, to the preparation and intermediates for the preparation thereof, and to compositions containing these compounds for controlling insects and representatives of the order Acarina, in particular plant-destructive feeding insects and ectoparasites that attack animals.

13 Claims, No Drawings

INSECTICIDAL 5-PYRIMIDINE CARBONITRILES

The present invention relates to novel substituted 2,4-diamino-5-cyanopyrimidines and salts and intermediates thereof, to the preparation of these compounds and to their use for controlling noxious insects and ectoparasites.

The novel compounds have the general formula I

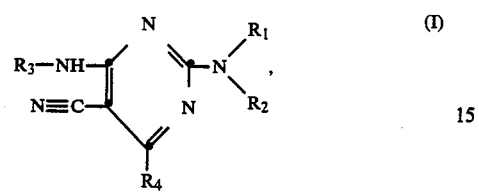

wherein $R_1$ is hydrogen, $C_1$-$C_6$alkyl, $C_2$-$C_6$alkenyl or $C_2$-$C_6$alkynyl, $R_2$ is hydrogen, $C_1$-$C_{10}$alkyl or $C_3$-$C_6$cycloalkyl, or $R_1$ and $R_2$, when taken together, are a radical selected from the group consisting of —(CH$_2$)$_3$—, —(CH$_2$)$_4$— and —(CH$_2$)$_5$, $R_3$ is hydrogen or a radical —CO—R$_5$ or —SO$_2$—R$_6$, $R_4$ is a radical selected from the group consisting of —NH$_2$, —NH—CO—R$_5$, —NH—SO$_2$—R$_6$,

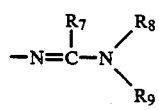

$R_5$ is hydrogen, $C_1$-$C_{12}$alkyl, $C_3$-$C_6$cycloalkyl, $C_1$-$C_6$alkoxy, perhalogenated $C_1$-$C_3$alkyl or the radical

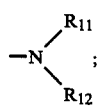

$R_6$ is $C_1$-$C_6$alkyl, $R_7$ is hydrogen or $C_1$-$C_6$alkyl, $R_8$ and $R_9$ are each independently of the other hydrogen or $C_1$-$C_6$alkyl or, when taken together, are a radical selected from the group consisting of —(CH$_2$)$_3$—, —(CH$_2$)$_4$— and —(CH$_2$)$_5$, $R_{10}$ is a radical —SO$_2$—R$_{13}$ or

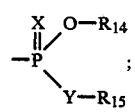

$R_{11}$ and $R_{12}$ are each independently of the other hydrogen or $C_1$-$C_6$alkyl or, when taken together, are a radical selected from the group consisting of —(CH$_2$)$_3$—, —(CH$_2$)$_4$— and —(CH$_2$)$_5$, $R_{13}$ is $C_1$-$C_{10}$alkyl, $C_1$-$C_{10}$alkyl which is substituted by up to 10 halogen atoms, or is $C_3$-$C_6$cycloalkyl $R_{14}$ and $R_{15}$ are each independently of the other $C_1$-$C_{10}$alkyl; and X and Y are each independently of the othe oxygen or sulfur, and salts thereof.

Within the scope of this invention, halogen atoms and halogen substituents will be understood as meaning fluorine, chlorine, bromine or iodine, with fluorine and chlorine being preferred.

On account of their advantageous properties, preferred compounds of formula I are those wherein $R_1$ is hydrogen or $C_1$-$C_4$alkyl, $R_2$ is $C_1$-$C_4$alkyl or $C_3$-$C_6$cycloalkyl, or $R_1$ and $R_2$ together are —(CH$_2$)$_4$— or —(CH$_2$)$_5$—, $R_3$ is hydrogen, $R_4$ is a radical —NH$_2$ or —NH—CO—R$_5$, $R_5$ is $C_1$-$C_4$alkyl or perhalogenated $C_1$-$C_3$alkyl, and salts thereof; as well as compounds of formula I, wherein $R_1$ is hydrogen, methyl or ethyl, $R_2$ is $C_1$-$C_4$alkyl or cyclopropyl, $R_3$ is hydrogen, $R_4$ is a radical —NH$_2$ or —NH—CO—R$_5$, $R_5$ is $C_1$-$C_3$alkyl, and salts thereof.

On account of their excellent pesticidal activity, particularly preferred compounds of formula I are those wherein $R_1$ is hydrogen, methyl or ethyl, $R_2$ is cyclopropyl, $R_3$ is hydrogen, and $R_4$ is a radical —NH$_2$ or —NH—CO—C$_2$—H$_5$, and salts thereof.

By salts of compounds of formula I are meant the physiologically tolerable addition salts of inorganic and organic acids. Examples of inorganic acids are hydrochloric acid, hydrobromic acid, hydriodic acid, sulfuric acid, phosphoric acid, phosphorous acid and nitric acid. Examples of organic acids are trifluoroacetic acid, trichloroacetic acid, formic acid, oxalic acid, succinic acid, maleic acid, lactic acid, glycolic acid, aconitic acid, citric acid, benzoic acid, benzenesulfonic acid and methanesulfonic acid.

The compounds of formula I can be prepared by (a) reacting a compound of formula II

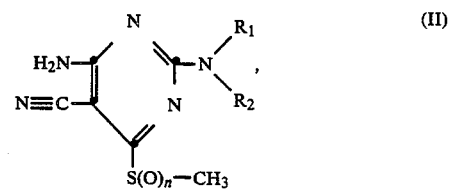

with ammonia, or (b) reacting a compound of formula III

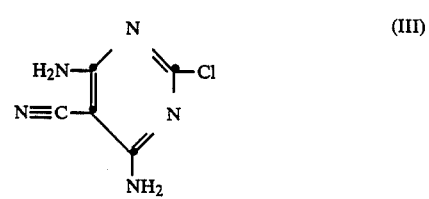

with an amine of formula IV

(IV)

and, if desired, converting the resultant compound of formula I, wherein $R_3$ is hydrogen and $R_4$ is the radical —$NH_2$ (compound Ia)

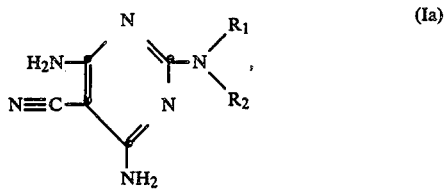
(Ia)

in a manner known per se, into a compound of formula I, wherein $R_3$ is —CO—$R_5$ or —$SO_2$—$R_6$ and/or $R_4$ is

—NH—CO—$R_5$, —NH—$SO_2$—$R_6$,

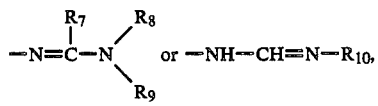 or —NH—CH=N—$R_{10}$, wherein $R_1$ to $R_{15}$, X and Y are as defined above and n is 0, 1 or 2, and, if desired, converting a resultant compound of formula I into a salt thereof.

In process variant (a), the reaction of a sulfonyl compound (n=2) of formula II with ammonia is generally carried out in the temperature range from about 10° to 100° C. in an organic solvent such as acetonitrile, tetrahydrofuran, dioxane or a solvent/water mixture. The same reaction conditions apply to process variant (b), in which the 2-chloro-4,6-diamino-5-cyanopyrimidine of formula III is reacted with an amine of formula IV. If a methylthio compound (n=0) is used as starting material in process variant (a), then the reaction with ammonia is preferably carried out in an autoclave under elevated pressure in the temperature range from 100° to 170° C., usually at about 160° C.

The conversion of a compound of formula I, wherein $R_4$ is —$NH_2$, into a compound in which $R_4$ has another meaning as indicated herein, can be effected by reaction of the amino group in 6-position of the pyrimidine ring with appropriate reactants which are known per se. Thus, for example, a 6-aminopyrimidine of formula I can be reacted with compounds of the Hal—CO—$R_5$, Hal—$SO_2$—$R_6$, ($R_5$—CO)$_2$O or $R_6O$—CH=N—$R_{10}$ type to give compounds of formula I which are suitably substituted in 6-position, where Hal is a halogen atom, preferably a chlorine atom, and $R_5$, $R_6$ and $R_{10}$ have the given meanings. If it is desired to prepare a compound of formula I, wherein $R_4$ is the radical

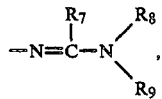

the 6—$NH_2$ group is reacted with e.g. an acetal of formula

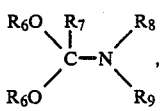

where $R_6$, $R_7$, $R_8$ and $R_9$ have the given meanings. In analogous manner and using appropriate reactants it is possible to prepare compounds of formula I, wherein $R_3$ is a radical —CO—$R_5$ or —$SO_2$—$R_6$, from 4-aminopyrimidines of formula I, wherein $R_3$ is hydrogen. The above described acylation reactions are carried out under normal pressure in inert solvents or diluents under normal pressure and in the presence of a base in the temperature range from 0° to 120° C., preferably from 40° to 80° C. Examples of suitable solvents and diluents are: alkanes such as n-pentane as well as homologs thereof, including isomers up to n-heptadecane; ethers such as diethyl ether, dipropyl ether, dibutyl ether, dimethoxyethane, dioxane or tetrahydrofuran; chlorinated hydrocarbons such as chloroform, methylene chloride, carbon tetrachloride or chlorobenzene; aromatic hydrocarbons such as benzene, toluene or xylenes. Further inert solvents and diluents may also be suitably used in the process of this invention. Possible bases which may be suitably used in these reactions are e.g. alkylamines such as triethylamine or diisopropylethylamine, as well as pyridine or N-methylpyrrolidone.

The starting compounds of formula II are novel and likewise constitute an object of the present invention, especially because they also have good pesticidal, in particular insecticidal, properties. They can be prepared as follows:

(a) For example, a compound of formula II, wherein n=0, can be prepared in accordance with the following reaction scheme:

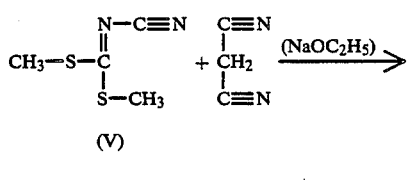
(V)

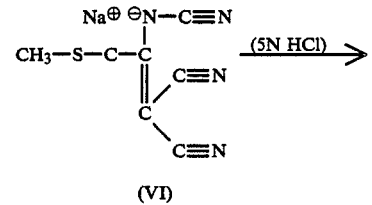
(VI)

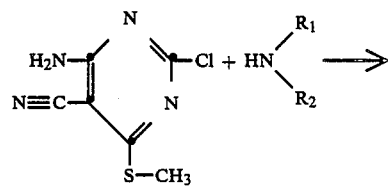
(VII)    (IV)

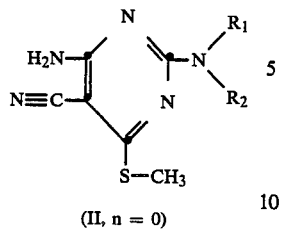

(II, n = 0)

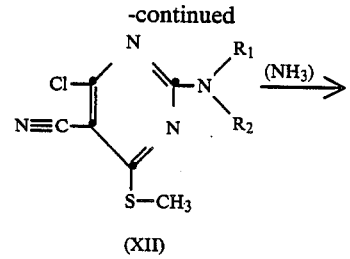

(XII)

Dimethyl N-cyanodithiocarboximidates of formula V used as starting materials for the above process and the salt of formula VI formed by reaction with malonitrile are known (q.v. Rec. Trav. Ch. 90/1971, 463; J. Chem. Soc., Chem. Comm. 1974, 350). A compound of formula II, wherein n=0, can be obtained from the salt of formula VI by cyclisation with 5N HCl and subsequent reaction of the resultant pyrimidine of formula VII with a corresponding amine of formula IV.

(b) In addition, compounds of formula II, wherein n=0, can be obtained as follows:

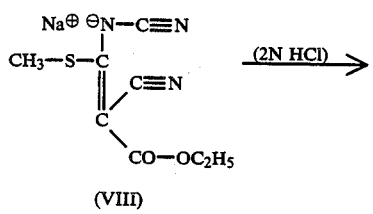

(VIII)

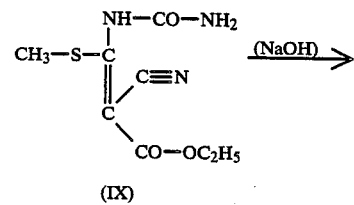

(IX)

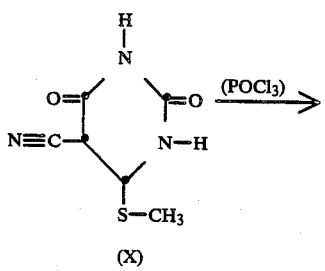

(X)

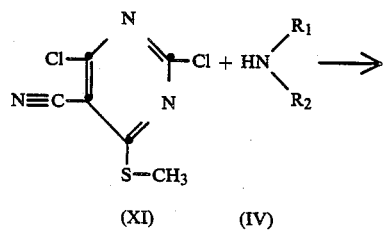

(XI)    (IV)

(II, n = 0)

The sodium salt of formula VIII indicated in the above reaction scheme, the urea of formula IX and the uracil of formula X are known (q.v. J. Chem. Soc., Chem. Comm. 1974, 350; Helv. Chim. Act. 1985, 1155). The preparation of the novel substituted pyrimidines of formulae XI and XII is carried out in a manner known per se. Reaction of XII with ammonia gives a compound of formula II, wherein n=0.

(c) Starting compounds of formula II, wherein n=1 or 2, can be prepared in a manner known per se by oxidation of compounds of formula II, wherein n=0 (q.v. "The Chemistry of Heterocyclic Compounds", Vol. 16: Pyrimidines, Intersc. Publ. Inc., N.Y. 1959).

The starting compound of formula III, i.e. 2-chloro-4,6-diamino-5-cyanopyrimidine, is known from Chem. Ber. 1968, 1244, but can be prepared in accordance with the following reaction scheme from the above compound of formula VII by oxidation to the sulfone and replacement of —SO$_2$CH$_3$ by —NH$_2$ by reaction with ammonia:

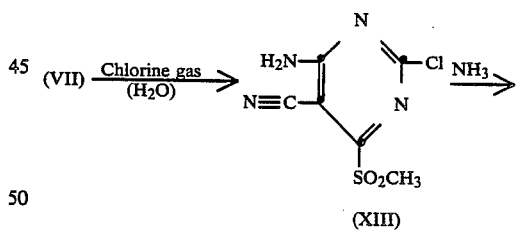

(XIII)

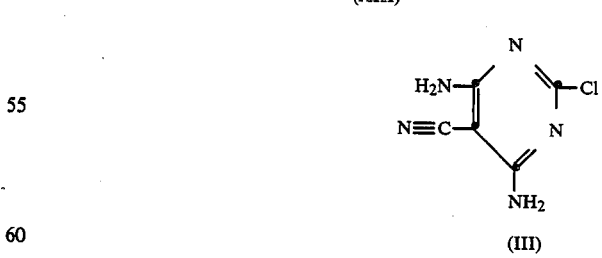

(III)

Pesticidal, especially insecticidal, 2,4,6-triamino-5-nitropyrimidines, the amino groups of which may be substituted, are already known from European patent application No. 0084.758. The compounds of formulae I and II differ structurally from these known compounds materially in that they contain the cyano group in 5-position.

Surprisingly, it has been found that the compounds of formulae I and II and salts thereof have excellent properties as pesticides while being well tolerated by plants and having low toxicity to warm-blooded animals. They are particularly suitable for controlling insects and representatives of the order Acarina that attack plants and animals.

In particular, the compounds of formulae I and II are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families: Ixodidae, Argasidae, Tetranychidae and Dermanyssidae.

In addition to their action against flies, e.g. Musca domestica, and mosquito larvae, the compounds of this invention are also suitable for controlling plant-destructive feeding insects in ornamentals and crops of useful plants, especially in cotton (e.g. against Spodoptera littoralis and Heliothis virescens) and in fruit and vegetables (e.g. against Plutella xylostella, Laspeyresia pomonella, Leptinotarsa decemlineata and Epilachna varivestis). The compounds of formulae I and II are also effective against rice pests. The compounds of formulae I and II have also a pronounced ovicidal and, in particular, larvicidal action against insects, especially against larvae of noxious feeding insects. If the active compounds of are ingested by adult insect stages with the feed, then a diminished oviposition and/or reduced hatching rate is observed in many insects, especially in Coleopterae, e.g. Anthonomus grandis.

The compounds of formulae I and II can also be used for controlling ectoparasites such as Lucilia sericata, in domestic animals and productive livestock, e.g. by treating animals, cowsheds, barns, stables, etc., and pastures.

In the treatment of graving animals with the compounds of this invention, for example by means of cattle dips, pour-on methods or spray races, the surprising adhesive action of the active substances provides a long-lasting toxic effect against ectoparasites, e.g. harmful Diptera, on the skin and fur of the animals. This prevents the active substances which have been applied to the skin or fur of productive livestock from being prematurely washed out or washed off by rainwater as it drips off the animals.

A particular advantage of the compounds of the invention resides in their oral administration to productive livestock. In this method of application the active ingredients exhibit an effective and prolonged insecticidal activity, in particular in the faeces excreted from the alimentary canal. Consequently, infestation by harmful insects, in particular Diptera, can be prevented before the pests occur in the vicinity of the animals, e.g. in livestock buildings, in enclosures and on grazing land, as the Diptera larvae hatching from the deposited eggs are killed immediately. A particularly important feature of this special form of application is that, by virtue of their structural properties, the compounds of formula I are physiologically harmless to warm-blooded animals. This method of selectively controlling the proliferation of insects is considerably more efficient and at the same time more economical than the customary methods of treating livestock buildings and enclosures on a large scale.

The good pesticidal activity of the compounds of formulae I and II corresponds to a mortality of at least 50-60% of the above pests.

The activity of the compounds of the invention and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of the invention are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or II combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna 1981.

The pesticidal compositions usually contain 0.1 to 99%, preferably 0.1 to 95%, of active ingredient or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1

(a) Preparation of the starting compound: 2-cyclopropylamino-4-amino-5-cyano-6-methylthiopyrimidine (i) While cooling with ice water, 650 ml of concentrated hydrochloric acid are added dropwise to a solution of 93 g of 2-cyano-3-cyanoamino-3-methylthioacrylonitrile, sodium salt, in 425 ml of water. The batch is then stirred for about 12 hours at room temperature. The precipitate is isolated by filtration and treated with aqueous sodium carbonate solution. 20 g of the resultant 2-chloro-4-amino-5-cyano-6-methylthiopyrimidine (m.p. 268° C.) are stirred in 250 ml of acetonitrile to a suspension to which, with vigorous stirring, 11.4 g of cyclopropylamine are added dropwise at reflux temperature. The batch is stirred for a further 12 hours and then water is added. The precipitate is isolated by filtration, affording the title compound of formula

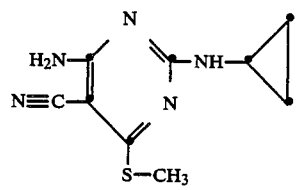

with a melting point of 215°–218° C. (compound 3.1).

(ii) 20 g of N,N-diethylaniline are slowly added dropwise to a mixture of 18.3 g of 5-cyano-6-methylthiouracil and 80 ml of phosphoroxy chloride. The batch is then refluxed for 1½ hours and subsequently concentrated by evaporation. The residue is mixed with 200 ml of ice-water, stirred, collected by filtration and washed with water. After drying, the crude product is chromatographed through a column of silica gel (elution with a 6:3:1 mixture of toluene/chloroform/ethyl acetate). 22 g of the resultant 2,4-dichloro-5-cyano-6-methylthiopyrimidine (m.p. 118°–120° C.) are dissolved in 200 ml of acetonitrile and a solution of 11.4 g of cyclopropylamine in 40 ml of acetonitrile is added at −10° C. The reaction mixture is stirred for 2 hours at room temperature and then poured into 2 liters of ice-water. The precipitate is filtered with suction. 26.1 g of the 2-cyclopropylamino-4-chloro-5-cyano-6-methylthiopyrimidine so obtained of formula

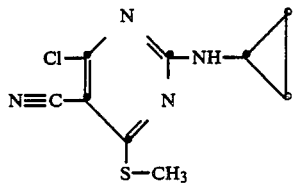

with a melting point of 139°–141° C. are stirred in 100 ml of acetonitrile. Then 300 ml of 30% aqueous ammonia are added to the suspension, which is then stirred for about 10 hours at room temperature and thereafter for 5 hours under reflux. The solid residue obtained from the cooled batch is filtered with suction and washed with water. Recrystallisation from 150 ml of methyl cellosolve affords the title compound of the formula indicated under (i) with a melting point of 215°–218° C.

(b) Preparation of 2-cyclopropylamino-4,6-diamino-5-cyanopyrimidine 33.7 g of the 2-cyclopropylamino-4-amino-5-cyano-6-methylthiopyrimidine prepared in accordance with (a) are reacted with 150 g of ammonia in an autoclave at 150° C. for 15–20 hours. The reaction product is stirred repeatedly in water and then isolated by filtration, affording the title compounds of formula

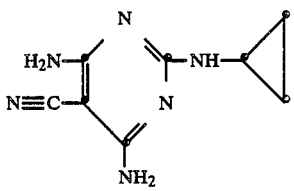

with a melting point of 249°–251° C. (compound 1.1).

EXAMPLE 2

(a) Preparation of the starting compound: 2-diethylamino-4-amino-5-cyano-6-methylsulfonylpyrimidine A reaction vesses is charged with 47.5 g of 2-diethylamino-4-amino-5-cyano-6-methylthiopyrimidine in 650 ml of methylene chloride. Without cooling, 88.7 g of 3-chloroperbenzoic acid are added to the batch. The reaction mixture is stirred for 2 hours and then filtered. The filtrate is concentrated by evaporation and the residue is suspended in diethyl ether and filtered with suction affording the title compound of formula

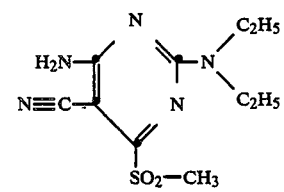

with a melting point of 170°–172° C. (compound 3.2).

(b) Preparation of 2-diethylamino-4,6-diamino-5-cyanopyrimidine 26.9 g of the 2-diethylamino-4-amino-5-cyano-6-methylsulfonylpyrimidine prepared in accordance with (a) are added to a mixture of 300 ml of 30% aqueous ammonia and 100 ml of acetonitrile. The batch is then kept under reflux for 12 hours, cooled, and the precipitate is isolated by filtration. The precipitate is stirred in water and filtered with suction, affording the title compound of formula

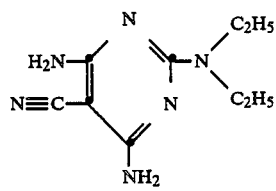

with a melting point of 222°–224° C. (compound 1.2).

EXAMPLE 3

Preparation of 2-diethylamino-4-amino-5-cyano-6-isobutyrylaminopyrimidine 7 g of triethylamine are added to a solution of 10.3 g of 2-diethylamino-4,6-diamino-5-cyanopyrimidine (prepared in accordance with Example 2) in 90 ml of tetrahydrofuran. Then 8.5 g of isobutyryl anhydride are added dropwise to this solution at 60° C. The reaction mixture is heated for 48 hours under reflux, concentrated by evaporation, and the residue is washed with diethyl ether, affording the title compound of formula

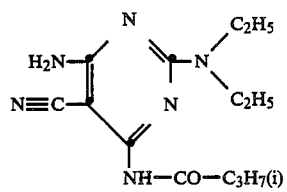

with a melting point of 151°–152° C. (compound 1.3).

EXAMPLE 4

Preparation of N,N-dimethyl-N'-(2-cyanopropylamino-4-amino-5-cyanopyrimidin-6-yl)formamidine 3.7 g of dimethylformamide diethyl acetal are added dropwise at 45°–50° C. to a solution of 3.8 g of 2-cyclopropylamino-4,6-diamino-5-cyanopyrimidine in 100 ml of dioxane. The reaction mixture is stirred for 8 hours at 45°–50° C. The solvent is removed by distillation and the crude product is recrystallised from ethanol, to give the title compound of formula

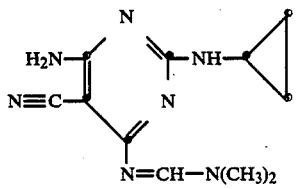

with a melting point of 192°–195° C. (compound 1.4).

EXAMPLE 5

Preparation of the starting compound: 2-chloro-4,6-diamino-4-amino-5-cyano-6-methylthiopyrimidine A reaction vessel is charged at 0° C. with a suspension of 50 g of finely powdered 2-chloro-4-amino-5-cyano-6-methylthiopyrimidine in 750 ml of dioxane and 250 ml of water. With stirring and without cooling, a strong stream of chlorine gas is passed into this suspension. A clear solution forms after about 20 minutes. The introduction of chlorine is complete after a further 30 minutes and the batch is stirred for ½ hour. The reaction mixture is concentrated by evaporation and the residue is suspended in 600 ml of ice-water and the suspension is filtered. 46.4 g of the residual 2-chloro-4-amino-5-cyano-6-methylsulfonylpyrimidine (m.p. 253° C. with dec.) are stirred in 25 g of 30% aqueous ammonia solution and 1000 ml of acetonitrile at room temperature for 2 hours. The batch is concentrated by evaporation, the residue is suspended in water and the suspension is filtered, affording the title compound of formula

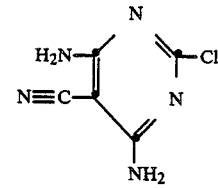

with a melting point of >260° C. (compound 5.1).

The following compounds of formula I are also prepared in accordance with the procedures described above:

| Compound | $R_1$ | $R_2$ | $R_3$ | $R_4$ | m.p. [°C.] |
|---|---|---|---|---|---|
| 1.5 | H | —$C_3H_7$(i) | H | —$NH_2$ | 230–232 |
| 1.6 | H | —CH($CH_3$)—$C_2H_5$ | H | —$NH_2$ | 195–197 |
| 1.7 | —$CH_3$ | —$CH_3$ | H | —$NH_2$ | >260 |
| 1.8 | —$C_3H_7$(n) | —$C_3H_7$(n) | H | —$NH_2$ | 204–206 |
| 1.9 | —$C_4H_9$(n) | —$C_4H_9$(n) | H | —$NH_2$ | 182–185 |
| 1.10 | —$CH_3$ | —$C_2H_5$ | H | —$NH_2$ | 250–251 |
| 1.11 | | —$(CH_2)_4$— | H | —$NH_2$ | >260 |
| 1.12 | | —$(CH_2)_5$— | H | —$NH_2$ | 234–236 |
| 1.13 | H | —$C(CH_3)_3$ | H | —$NH_2$ | 180–183 |
| 1.14 | —$CH_3$ | —$C_4H_9$(n) | H | —$NH_2$ | 194–196 |
| 1.15 | H | cyclopropyl | H | —NH—CO—$CH(CH_3)_2$ | 215–218 |
| 1.16 | H | cyclopropyl | H | —NH—CO—$C_2H_5$ | 180–181 |
| 1.17 | H | cyclopropyl | H | —NH—CO—$CH_3$ | 203–205 |
| 1.18 | —$C_2H_5$ | —$C_2H_5$ | H | —NH—CO—$C_2H_5$ | 158–160 |
| 1.19 | —$C_2H_5$ | —$C_2H_5$ | H | —NH—CO—$C(CH_3)_3$ | 113–115 |
| 1.20 | —$C_2H_5$ | —$C_2H_5$ | H | —NH—CO—$CH_3$ | 168–171 |
| 1.21 | —$C_2H_5$ | —$C_2H_5$ | H | —NH—CO—$C_3H_7$(n) | 149–150 |
| 1.22 | H | cyclopropyl | H | —NH—CO—$C(CH_3)_3$ | 110–113 |
| 1.23 | —$C_2H_5$ | —$C_2H_5$ | H | —NH—CO—$C_4H_9$(n) | 119–120 |
| 1.24 | H | cyclopropyl | H | —NH—CO—$C_3H_7$(n) | 175–176 |
| 1.25 | H | cyclopropyl | H | —NH—CO—$C_4H_9$(n) | 187–188 |
| 1.26 | —$C_2H_5$ | —$C_2H_5$ | H | —NH—CO—$CF_3$ | 190–191 |
| 1.27 | H | cyclopropyl | H | —NH—CO—$CF_3$ | 268 |

-continued

| Compound | R₁ | R₂ | R₃ | R₄ | m.p. [°C] |
|---|---|---|---|---|---|
| 1.28 | —CH₃ | —C₄H₉(n) | H | —NH—CO—CH(CH₃)₂ | 139–140 |
| 1.29 | —CH₃ | —C₂H₅ | H | —NH—CO—CH(CH₃)₂ | 146–149 |
| 1.30 | H | cyclopropyl | H | —NH—CO—CH(C₂H₅)₂ | 196–197 |
| 1.31 | —C₂H₅ | —C₂H₅ | H | —NH—CO—(CH₂)₄CH₃ | 133–135 |
| 1.32 | H | cyclopropyl | H | —NH—CO—(CH₂)₄CH₃ | 170–173 |
| 1.33 | H | cyclopropyl | H | —N=CH—N(CH₃)—CH₃ | 192–195 |
| 1.34 | —C₂H₅ | H | | —N=CH—N(CH₃)—CH₃ | 160–165 |
| 1.35 | H | cyclopropyl | H | —N=CH—NH—SO₂CH₃ | 203–205 |
| 1.36 | —C₂H₅ | —C₂H₅ | J | —N=CH—NH—SO₂CH₃ | 182–185 |
| 1.37 | —C₂H₅ | —C₂H₅ | H | —N=CH—NH—P(=O)(OC₂H₅)(SC₃H₇(n)) | 127–128 |
| 1.38 | —CH₃ | —CH₂—CH=CH₂ | H | —NH₂ | 199–201 |
| 1.39 | H | —CH₂—CH=CH₂ | H | —NH₂ | 191–193 |
| 1.40 | H | —CH₂—C≡CH | H | —NH₂ | >260 |
| 1.41 | H | —CH₂—cyclopropyl | H | —NH₂ | 228–229 |
| 1.42 | H | cyclopropyl | —CO—CH₃ | —NH—CO—CH₃ | ~260 |
| 1.43 | —C₂H₅ | —C₂H₅ | —CO—CH₃ | —NH—CO—CH₃ | 263–265 |

The following salts of formula I are prepared by reaction with the respective acids:

| Compound | R₁ | R₂ | —NHR₃ | R₄ | Acid | m.p. [°C] |
|---|---|---|---|---|---|---|
| 2.1 | H | cyclopropyl | —NH₂ | —NH₂ | HCl | 210 (dec.) |
| 2.2 | H | cyclopropyl | —NH₂ | —NH₂ | F₃C—COOH | 209–210 |

-continued

| Compound | $R_1$ | $R_2$ | $-NHR_3$ | $R_4$ | Acid | m.p. [°C.] |
|---|---|---|---|---|---|---|
| 2.3 | H | △ | $-NH_2$ | $-NH_2$ | $(COOH)_2$ | 198 (dec.) |
| 2.4 | $-C_2H_5$ | $-C_2H_5$ | $-NH_2$ | $-NH_2$ | HCl | 167–169 |
| 2.5 | $-C_2H_5$ | $-C_2H_5$ | $-NH_2$ | $-NH_2$ | $F_3C-COOH$ | 175–178 |
| 2.6 | $-C_2H_5$ | $-C_2H_5$ | $-NH_2$ | $-NH_2$ | $(COOH)_2$ | 178–188 |
| 2.7 | H | △ | $-NH_2$ | $-NH-CO-CH(CH_3)_2$ | HCl | ~140 |
| 2.8 | H | △ | $-NH_2$ | $-NH-CO-CH(CH_3)_2$ | $CF_3COOH$ | 150–153 |
| 2.9 | H | △ | $-NH_2$ | $-NH_2$ | $H_3PO_4$ | 208 |
| 2.10 | H | △ | $-NH_2$ | $-NH_2$ | $H_2SO_4$ | 188 |
| 2.11 | $-C_2H_5$ | $-C_2H_5$ | $-NH_2$ | $-NH_2$ | $H_2SO_4$ | 199–201 |
| 2.12 | $-C_2H_5$ | $-C_2H_5$ | $-NH_2$ | $-NH_2$ | $H_3PO_4$ | 185 |
| 2.13 | $-C_2H_5$ | $-C_2H_5$ | $-NH_2$ | $-NH_2$ | $CH_3SO_3H$ | 205–207 |
| 2.14 | H | △ | $-NH_2$ | $-NH_2$ | $CH_3SO_3H$ | 250 |
| 2.15 | $-C_2H_5$ | $-C_2H_5$ | $-NH_2$ | $-NH_2$ | maleic acid | 150 |
| 2.16 | H | △ | $-NH_2$ | $-NH_2$ | maleic acid | 185 |
| 2.17 | $-C_2H_5$ | $-C_2H_5$ | $-NH_2$ | $-NH_2$ | malonic acid | 216–220 |
| 2.18 | H | △ | $-NH_2$ | $-NH_2$ | $HNO_3$ | 163 |
| 2.19 | $-C_2H_5$ | $-C_2H_5$ | $-NH_2$ | $-NH_2$ | $HNO_3$ | 179 |
| 2.20 | H | △ | $-NH_2$ | $-NH_2$ | malonic acid | >230 |

The following compounds of formula I can also be prepared as described above:

| $R_1$ | $R_2$ | $R_3$ | $R_4$ |
|---|---|---|---|
| H | $-CH_3$ | H | $-NH_2$ |
| H | $-C_2H_5$ | H | $-NH_2$ |
| H | $-C_3H_7(n)$ | H | $-NH_2$ |

-continued

| R₁ | R₂ | R₃ | R₄ |
|---|---|---|---|
| H |  | H | —NH₂ |
| H | 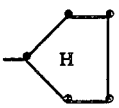 | H | —NH₂ |
| H | 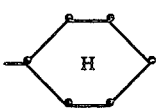 | H | —NH₂ |
| H | —CH(C₂H₅)₂ | H | —NH₂ |
| —C₃H₇(i) | —C₃H₇(i) | H | —NH₂ |
| H |  | H | —N=CH—NH—P(=O)(OC₂H₅)(SC₃H₇(n)) |
| H |  | H | —NH—CO—O—C₂H₅ |
| —C₂H₅ | —C₂H₅ | H | —NH—CO—O—C₂H₅ |
| —C₂H₅ | —C₂H₅ | H | —NH—CO—CH₂Cl |
| H |  | H | —NH—CO—C₂F₅ |
| —C₂H₅ | —C₂H₅ | H | —NH—CO—C₂F₅ |
| H |  | H | —NH—CO—C₃F₇(n) |
| —C₂H₅ | —C₂H₅ | H | —NH—CO—C₃F₇(n) |
| H |  | —CO—C₂H₅ | —NH—CO—C₂H₅ |
| H |  | —CO—C₃H₇(n) | —NH—CO—C₃H₇(n) |
| H |  | —CO—CH(CH₃)₂ | —NH—CO—CH(CH₃)₂ |
| —C₂H₅ | —C₂H₅ | —CO—C₂H₅ | —NH—CO—C₂H₅ |
| —C₂H₅ | —C₂H₅ | —CO—C₃H₇(n) | —NH—CO—C₃H₇(n) |
| —C₂H₅ | —C₂H₅ | —CO—CH(CH₃)₂ | —NH—CO—CH(CH₃)₂ |
| H |  | —CO—CF₃ | —NH—CO—CF₃ |
| —C₂H₅ | —C₂H₅ | —CO—CF₃ | —NH—CO—CF₃ |

-continued

| R₁ | R₂ | R₃ | R₄ |
|---|---|---|---|
| H | (cyclopropyl) | —CO—CH₃ | —NH—CO—CH(CH₃)₂ |
| —C₂H₅ | —C₂H₅ | —CO—C₂H₅ | —NH—CO—CH(CH₃)₂ |

The following intermediates of formula II are prepared as described above:

| Compound | R₁ | R₂ | R₃ | n | m.p. [°C.] |
|---|---|---|---|---|---|
| 3.3 | H | —CH₃ | H | 0 | 270–274 |
| 3.4 | H | —C₃H₇(i) | H | 0 | 171–173 |
| 3.5 |  | —(CH₂)₄— | H | 0 | 198–200 |
| 3.6 |  | —(CH₂)₅— | H | 0 | 204–206 |
| 3.7 | H | —C(CH₃)₃ | H | 0 | 194–196 |
| 3.8 | H | —CH(CH₃)—C₂H₅ | H | 0 | 143–145 |
| 3.9 | H | —CH(C₂H₅)₂ | H | 0 | 151–153 |
| 3.10 | —CH₃ | —CH₃ | H | 0 | 216–218 |
| 3.11 | —C₂H₅ | —C₂H₅ | H | 0 | 131 |
| 3.12 | —CH₃ | —C₂H₅ | H | 0 | 158–160 |
| 3.13 | —CH₃ | —C₄H₉(n) | H | 0 | 158–160 |
| 3.14 | —C₃H₇(n) | —C₃H₇(n) | H | 0 | 160–162 |
| 3.15 | —C₄H₉(n) | —C₄H₉(n) | H | 0 | 120–122 |
| 3.16 | H | H | H | 0 | ~270 (dec.) |
| 3.17 | H | (cyclopropyl) | H | 2 | 167–170 |
| 3.18 | —CH₃ | —CH₃ | H | 2 | 237–239 |
| 3.19 | —C₃H₇(n) | —C₃H₇(n) | H | 2 | 222–225 |
| 3.20 | —C₄H₉(n) | —C₄H₉(n) | H | 2 | 165–167 |
| 3.21 | —CH₃ | —C₂H₅ | H | 2 | 203–205 |
| 3.22 |  | —(CH₂)₄— | H | 2 | 235–237 |
| 3.23 |  | —(CH₂)₅— | H | 2 | 204–207 |
| 3.24 | —CH₃ | —C₄H₉(n) | H | 2 | 190–191 |

The following intermediates of formula II can be prepared as described above:

| R₁ | R₂ | R₃ | n |
|---|---|---|---|
| H | —C₂H₅ | H | 0 |
| H | —C₃H₇(n) | H | 0 |
| H | —C₃H₇(i) | H | 0 |
| H | —CH(C₂H₅)₂ | H | 0 |
| H | (cyclobutyl) | H | 0 |
| H | (cyclopentyl-H) | H | 0 |
| H | (cyclohexyl-H) | H | 0 |
| H | —CH(CH₃)—C₂H₅ | H | 0 |
| —CH₃ | —CH₃ | H | 0 |
| —C₃H₅ | —C₂H₅ | H | 0 |
| H | —CH₃ | H | 2 |
| H | —C₂H₅ | H | 2 |
| H | —C₃H₇(n) | H | 2 |
| —C₃H₇(i) | —C₃H₇(i) | H | 2 |
| H | (cyclobutyl) | H | 2 |
| H | (cyclopentyl-H) | H | 2 |
| H | (cyclohexyl-H) | H | 2 |
| H | —CH(CH₃)—C₂H₅ | H | 2 |
| H | —CH(C₂H₅)₂ | H | 2 |

The following intermediates of formula IX are prepared as described above:

| Compound | R₁ | R₂ | m.p. [°C.] |
|---|---|---|---|
| 4.1 | H | —CH₃ | 270–274 |
| 4.2 | H | —C₃H₇(i) | 171–173 |
| 4.3 | H | (cyclopropyl) | 215–218 |
| 4.4 | H | —CH(CH₃)—C₂H₅ | 143–145 |
| 4.5 | H | —CH(C₂H₅)₂ | 151–153 |
| 4.6 | —CH₃ | —CH₃ | 216–218 |
| 4.7 | —C₂H₅ | —C₂H₅ | 131 |
| 4.8 | —C₃H₇(n) | —C₃H₇(n) | 160–162 |
| 4.9 | —C₄H₉(n) | —C₄H₉(n) | 120–122 |
| 4.10 | H | H | 270 (dec.) |
| 4.11 | —CH₃ | —C₂H₅ | 158–160 |
| 4.12 | H | —C(CH₃)₃ | 194–196 |
| 4.13 |  | —(CH₂)₄— | 198–200 |
| 4.14 |  | —(CH₂)₅— | 204–206 |
| 4.15 | —CH₃ | —C₄H₉(n) | 158–160 |

The following intermediates of formula XI can also be prepared as described

| R₁ | R₂ |
|---|---|
| H | —C₂H₅ |
| H | —C₃H₇(n) |
| H | (cyclobutyl) |

-continued

| R₁ | R₂ |
|---|---|
| H | 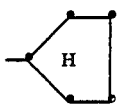 |
| H | 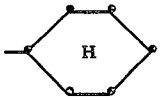 |
| —C₃H₇(i) | —C₃H₇(i) |

EXAMPLE 6

Formulations for active ingredients according to Examples 1 to 3 or combinations thereof with other insecticides or acaricides (throughout, percentages are by weight)

| 1. Wettable powders | (a) | (b) | (c) |
|---|---|---|---|
| active ingredient or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| active ingredient or combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| active ingredient or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| active ingredient or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| active ingredient or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| active ingredient or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

| 7. Pour-on solution | |
|---|---|
| active ingredient | 30.00 g |
| sodium dioctylsulfosuccinate | 3.00 g |
| benzyl alcohol | 35.46 g |
| ethylene glycol monomethyl ether | 35.46 g |
| | 103.92 g = 100 ml |

With vigorous stirring, the active ingredient is dissolved in the bulk of the mixture of the two solvents. The sodium dioctylsulfosuccinate is subsequently dissolved in the resultant solution, with heating if necessary, and the rest of the solvent mixture is added.

EXAMPLE 7

Action against Musca domestica 50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of Musca domestica are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formulae I and II according to Examples 1 to 3 exhibit good activity in this test.

EXAMPLE 8

Action against Lucilia sericata 1 ml of an aqueous formulation containing 0.5% of test compound is added at 50° C. to 9 ml of a culture medium. Then about 30 freshly hatched Lucilia sericata larvae are added to the culture medium, and the insecticidal action is determined after 48 and 96 hours by evaluating the mortality rate.

In this test, compounds of formulae I and II according to Examples 1 to 3 exhibit good activity against Lucilia sericata.

EXAMPLE 9

Action against Lucilia cuprina

Freshly deposited eggs of the blowfly (L. cuprina) are put in small portions (30–50 eggs) into each of a number of test tubes, in which 4 ml of nutrient medium have been mixed with 1 ml of test solution. After inoculation of the culture medium, the test tubes are sealed with cotton-wool plugs and are then incubated in an incubator at 30° C. for 4 days. In the untreated medium serving as control, larvae about 1 cm in length (stage 3) have developed by the end of this 4-day period. When a substance is active, by the end of this period the larvae are either dead or moribund.

Repellency is also taken into account, since this causes the larvae to migrate from the medium and consequently to starve to death.

In this test, compounds of formulae I and II according to Examples 1 to 3 are very effective against Lucilia cuprima.

EXAMPLE 10

Action against Aëdes aegypti

A concentration of 800 ppm is obtained by pipetting a specific amount of a 0.1% solution of the test compound in acetone onto the surface of 150 ml of water in a beaker. After the acetone has evaporated, 30 to 40 two-day old larvae of Aëdes aegypti are put into the beaker containing the test compound. Mortality counts are made after 1, 2 and 5 days.

In this test, compounds of formulae I and II according to Examples 1 to 3 exhibit good activity against Aëdes aegypti.

EXAMPLE 11

Insecticidal action against feeding insects

Cotton plants about 25 cm high, in pots, are sprayed with aqueous emulsions which contain the respective test compound in concentrations of 100, 200 and 400 ppm. After the spray coating has dried, the cotton plants are populated with Spodoptera littoralis and Heliothis virescens larvae in the $L_3$-stage. The test is carried out at 24° C. and 60% relative humidity. The percentage mortality of the larvae is determined after 2 days.

In the above test, compounds of 1.1 and 1.2 effect 80–100% kill against Spodoptera larvae at a concentration of 200 and 400 ppm respectively. Compounds 1.1 and 1.2 effect 80–100% kill against Heliothis larvae at a concentration of 100 ppm and 400 ppm respectively.

EXAMPLE 12

Action against Anthonomus grandis (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (Anthonomus grandis). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of formulae I and II according to Examples 1 to 3 exhibit good activity in this test.

EXAMPLE 13

Action against ticks (A) Amblyomma hebraeum 50 nymphs are counted into a test tube and immersed for 1 to 2 minutes in 2 ml of an aqueous emulsion prepared from a dilution series containing 400 ppm of test compound. The test tube is then sealed with a standard cotton wool plug and placed on its head to enable the cotton wool to absorb the emulsion. Evaluation is made 1 week later. Two replicates are carried out for each test compound.

(B) Boophilus microplus (larvae)

Tests are carried out with 20 OP-sensitive and 20 OP-resistant larvae using a dilution series similar to that used in Test A. (The resistance refers to the tolerance towards diazinone). In this test compounds of formulae I and II according to Examples 1 to 3 are very effective against nymphs and larvae of the ticks Ambylomma hebraeum and Boophilus microplus.

EXAMPLE 14

Insectidal action: Nilaparvata lugens

Rice plants are sprayed with a solution containing 400 ppm of test compound. After the spray coating has dried, the plants are populated with nymphs of Nilaparvata lugens in the $N_2$ or $N_3$ stage. Two plants are used per test compound and per test species. Evaluation of the mortality rate is made 6 days later. The test is carried out at 26° C. and 60% relative humidity. In this test, compound 1.1 is 80–100% effective against nymphs of Nilaparvata lugens.

EXAMPLE 15

Action against soil insects (Diabrotica balteata)

5 maize seedlings 1 to 3 cm in height and a filter paper disc are immersed in an aqueous solution of the test compound contaianing and about 4 vol.% of acetone. The immersed filter paper disc is placed on the bottom of a 200 ml plastic beaker. A dry filter paper disc together with the maize seedlings and 10 Diabrotica balteata larvae in the $L_2$- or $L_3$-stage are then placed on the first disc. The test is carried out at about 24° C. and at 40–60% relative humidity and in daylight. Evaluation is made 6 days later in comparison with untreated controls.

In this test, compound 1.15 effects 80–100% kill at a concentration of 400 ppm.

EXAMPLE 16

Action against Nephotettix cincticeps (nymphs)

The test is carried out with growing plants. For this purpose rice plants about 20 days old and about 15 cm in height are planted into each of a number of pots (diameter: 5.5 cm).

The plants in each pot are sprayed on a rotary table with 100 ml of an acetonic solution containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be resprayed at least once. The test is carried out at a temperature of about 23° C. and at 55% relative humidity. The plants are exposed to light for a period of 16 hours per day.

In this test, compound 1.1 according to Example 1 is 80–100% effective.

EXAMPLE 17

Insecticidal stomach poison action against Plutella xylostella

Potted Chinese cabbage plants (pot size: 10 cm diameter) in the 4-leaf stage are sprayed with aqueous emulsions which contain the test compound in concentrations of 3 to 400 ppm and which dry on the plants.

After 2 days, each treated Chinese cabbage plant is populated with 10 Plutella xylostella larvae in the $L_2$-stage. The test is carried out at 24° C. and at 60% relative humidity in dim light. After 2 and 5 days evaluation is made to determine the percentage mortality of the larvae.

Compounds of formula I according to Examples 1 to 4 effect 80–100% kill in this test.

What is claimed is:

1. A compound of formula

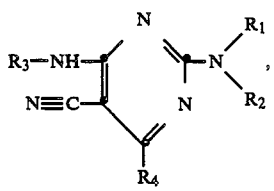

(I)

wherein $R_1$ is hydrogen, $C_1$-$C_6$alkyl, $C_2$-$C_6$alkenyl or $C_2$-$C_6$alkynyl, $R_2$ is hydrogen, $C_1$-$C_{10}$alkyl or $C_3$-$C_6$cycloalkyl, or $R_1$ and $R_2$, when taken together, are a radical selected from the group consisting of —(CH$_2$)$_3$—, —(CH$_2$)$_4$— and —(CH$_2$)$_5$, $R_3$ is hydrogen or a radical —CO—$R_5$ or —SO$_2$—$R_6$, $R_4$ is a radical selected from the group consisting of —NH$_2$, —NH—CO—$R_5$, —NH—SO$_2$—$R_6$,

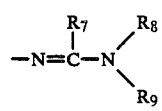

or —NH—CH=N—$R_{10}$;

$R_5$ is hydrogen, $C_1$-$C_{12}$alkyl, $C_3$-$C_6$cycloalkyl, $C_1$-$C_6$alkoxy, perhalogenated $C_1$-$C_3$alkyl or the radical

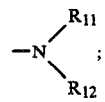

$R_6$ is $C_1$-$C_6$alkyl, $R_7$ is hydrogen or $C_1$-$C_6$alkyl, $R_8$ and $R_9$ are each independently of the other hydrogen or $C_1$-$C_6$alkyl or, when taken together, are a radical selected from the group consisting of —(CH$_2$)$_3$—, —(CH$_2$)$_4$— and —(CH$_2$)$_5$, $R_{10}$ is a radical —SO$_2$—$R_{13}$ or

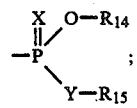

$R_{11}$ and $R_{12}$ are each independently of the other hydrogen or $C_1$-$C_6$alkyl or, when taken together, are a radical selected from the group consisting of —(CH$_2$)$_3$—, —(CH$_2$)$_4$— and —(CH$_2$)$_5$, $R_{13}$ is $C_1$-$C_{10}$alkyl which is substituted by up to 10 halogen atoms, or is $C_3$-$C_6$cycloalkyl $R_{14}$ and $R_{15}$ are each independently of the other $C_1$-$C_{10}$alkyl; and X and Y are each independently of the other oxygen or sulfur, or a salt thereof.

2. A compound according to claim 1 of formula I, wherein $R_1$ is hydrogen or $C_1$-$C_4$alkyl, $R_2$ is $C_1$-$C_4$alkyl or $C_3$-$C_6$cycloalkyl, or $R_1$ and $R_2$, when taken together, are a radical —(CH$_2$)$_4$ or —(CH$_2$)$_5$—, $R_3$ is hydrogen, $R_4$ is a radical —NH$_2$ or —NH—CO—$R_5$, $R_5$ is $C_1$-$C_4$alkyl or perhalogenated $C_1$-$C_3$alkyl, or a salt thereof.

3. A compound according to claim 2 of formula I, wherein $R_1$ is hydrogen, methyl or ethyl, $R_2$ is $C_1$-$C_4$alkyl or cyclopropyl, $R_3$ is hydrogen, $R_4$ is a radical —NH$_2$ or —NH—CO—$R_5$, $R_5$ is $C_1$-$C_3$alkyl, or a salt thereof.

4. A compound according to claim 3 of formula I, wherein $R_1$ is hydrogen, methyl or ethyl, $R_2$ is cyclopropyl, $R_3$ is hydrogen, and $R_4$ is a radical —NH$_2$ or —NH—CO—C$_2$—H$_5$, or a salt thereof.

5. A compound according to claim 4 of formula

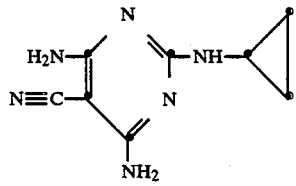

6. A compound according to claim 4 of formula

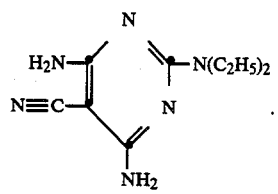

7. A compound according to claim 4 of formula

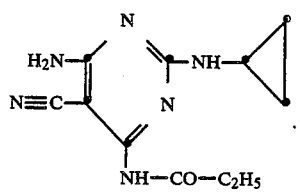

8. A compound according to claim 4 of formula

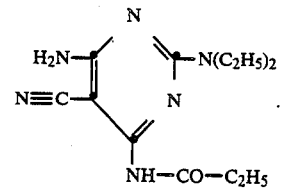

9. A pesticidal composition which comprises, as active component, a compound of formula I or II as claimed in any one of claims 1 to 8, or a salt thereof, together with suitable carriers and/or other adjuvants.

10. A method according to claim 1, of controlling insects and representatives of the order Acarina in animals or plants.

11. A method according to claim 1 of controlling larval stages of plant-destructive insects.

12. A method according to claim 1 of controlling ectoparasites of domestic animals and productive livestock.

13. A method of controlling pests selected from insects and representatives of the order Acarina, which comprises treating or contacting said pests, their various development stages or the locus thereof, with a pesticidally effective amount of a compound of formula I according to any one of claims 1 to 8 or 10, or with a salt thereof, together with adjuvants and carriers suitable therefor.

* * * * *